US012558359B2

(12) United States Patent
Hofmann et al.

(10) Patent No.: US 12,558,359 B2
(45) Date of Patent: Feb. 24, 2026

(54) COMPOSITION HAVING IMPROVED VOLUNTARY ACCEPTANCE

(71) Applicant: Elanco Animal Health GmbH, Monheim am Rhein (DE)

(72) Inventors: Stefan Hofmann, Langenfeld (DE); Venkata-Rangarao Kanikanti, Leverkusen (DE); Franziska Schmidt, Duesseldorf (DE); Sandra Mangold-Gehring, Solingen (DE); Annette Boegel, Leichlingen (DE); Brigitte Pommer, Wermelskirchen (DE)

(73) Assignee: Elanco Animal Health GmbH, Monheim am Rhein (DE)

( * ) Notice: Subject to any disclaimer, the term of this patent is extended or adjusted under 35 U.S.C. 154(b) by 580 days.

(21) Appl. No.: 17/916,195

(22) PCT Filed: Mar. 30, 2021

(86) PCT No.: PCT/EP2021/058295

§ 371 (c)(1),
(2) Date: Sep. 30, 2022

(87) PCT Pub. No.: WO2021/198256

PCT Pub. Date: Oct. 7, 2021

(65) Prior Publication Data

US 2023/0143264 A1 May 11, 2023

(30) Foreign Application Priority Data

Mar. 31, 2020 (EP) .................................... 20167444

(51) Int. Cl.

| | |
|---|---|
| ***A61K 9/00*** | (2006.01) |
| ***A61K 31/5377*** | (2006.01) |
| ***A61K 47/10*** | (2017.01) |
| ***A61K 47/12*** | (2006.01) |
| ***A61K 47/14*** | (2017.01) |
| ***A61K 47/44*** | (2017.01) |

(52) U.S. Cl.
CPC ........ *A61K 31/5377* (2013.01); *A61K 9/0053* (2013.01); *A61K 47/10* (2013.01); *A61K 47/12* (2013.01); *A61K 47/14* (2013.01); *A61K 47/44* (2013.01)

(58) Field of Classification Search
None
See application file for complete search history.

(56) References Cited

U.S. PATENT DOCUMENTS

| | | | | |
|---|---|---|---|---|
| 5,756,474 | A | 5/1998 | Furstenau | |
| 8,389,520 | B2 | 3/2013 | Thede et al. | |
| 8,647,690 | B2 * | 2/2014 | Corrigan | A23P 20/15 426/305 |
| 8,653,074 | B2 | 2/2014 | Militzer et al. | |
| 8,653,111 | B2 | 2/2014 | Thede et al. | |
| 8,658,683 | B2 | 2/2014 | Roach | |
| 8,987,261 | B2 | 3/2015 | Thede et al. | |
| 9,168,249 | B2 | 10/2015 | Thede et al. | |
| 9,533,972 | B2 | 1/2017 | Militzer et al. | |
| 2012/0076914 | A1 | 3/2012 | Langford | |
| 2012/0129857 | A1 * | 5/2012 | Militzer | A61P 9/00 544/122 |
| 2012/0141546 | A1 | 6/2012 | Kanikanti et al. | |
| 2016/0229858 | A1 | 8/2016 | Thede et al. | |
| 2023/0143264 | A1 | 5/2023 | Hofmann et al. | |

FOREIGN PATENT DOCUMENTS

| | | | |
|---|---|---|---|
| CN | 101919869 | A | 12/2010 |
| EP | 1320356 | B1 | 12/2007 |
| EP | 2155680 | B1 | 12/2013 |
| EP | 4126057 | A1 | 2/2023 |
| JP | H06508628 | A | 9/1994 |
| JP | 2004500392 | A | 1/2004 |
| JP | 2009526829 | A | 7/2009 |
| JP | 2010508299 | A | 3/2010 |
| JP | 2014500877 | A | 1/2014 |
| WO | 2008/067871 | A1 | 6/2008 |
| WO | 2010102762 | A1 | 9/2010 |
| WO | 2012/065967 | A1 | 5/2012 |
| WO | 2013167552 | | 11/2013 |
| WO | 2018/232227 | A1 | 12/2018 |

(Continued)

OTHER PUBLICATIONS

I.I. Krasnyuk, et al., “Pharmaceutical technology: Technology of dosage forms”, textbook for students of higher educational institutions, ed. I.I. Krasnyuk, G.V. Mikhailova.—M: Publishing center “Academy”, 2006.—592 p.-p. 8.

Raymond C Rowe, et al., “Handbook of Pharmaceutical Excipients. Sixth edition”, Edited by Raymond C Rowe, Paul J Sheskey and Marian E Quinn, Pharmaceutical Press and American Pharmacists Association. London, Chicago. 2009 (Thickening agents).

ФС.3.7.0001.18. Fish liver fatty oil. State Pharmacopoeia of the Russian Federation. XIV edition. vol. IV. Moscow, 2018.—pp. 6739-6761.-pp. 6739.

“Final Amended Report on the Safety Assessment of Mink Oil”, International Journal of Toxicology, 24 (Suppl. 3): 57-64, 2005. doi: 10.1080/10915810500257154.—p. 58, Table 1.

A.I. Tikhonov, et al., “Biopharmacy: Textbook for students of pharmaceutical universities and departments”, Ed. A.I. Tikhonov.—X.: NPU’s publishing house, Golden Pages, 2003.—240 p. 18 III.-p. 29-30.

(Continued)

*Primary Examiner* — Susan T Tran
(74) *Attorney, Agent, or Firm* — McBee Moore & Vanik IP, LLC

(57) ABSTRACT

The present invention relates to the field of pharmaceutical compositions suitable for the oral administration of an active in animals. In particular, the present invention relates to a liquid drug-containing formulation and to the use thereof. The present invention further relates to the use of a liquid formulation aid composition comprising at least one natural oil of herbal origin in a liquid drug-containing formulation for improving the acceptance or voluntary acceptance of drug intake in animal.

13 Claims, No Drawings

(56) References Cited

FOREIGN PATENT DOCUMENTS

| | | | |
|---|---|---|---|
| WO | 2019/028150 | A1 | 2/2019 |
| WO | 2021198256 | A1 | 10/2021 |

OTHER PUBLICATIONS

Yeh, T.-L., et al., "Molecular and cellular mechanisms of HIF prolyl hydroxylase inhibitors in clinical trials", Chem. Sci., 2017, 8, 7651-7668.
International Search Report of International Application No. PCT/EP2021/058295, mailed Jun. 7, 2021.
"General basics of chemical technology", Poland, 1973. Translation from Polish under ed. AM P.G. Romankova and PhD in engineering science M.I. Kurochkina. Chemistry, 1977. 504 pages.
Soldatenkov, et al.,"Applied stereochemistry of biologically active substances", Hanoi: Publishing house Knowledge, 2015, 326 pages.
Belikov V.G., "Pharmaceutical Chemistry", Textbook, 2007, Moscow, Medpress-inform, pp. 27-29.

* cited by examiner

COMPOSITION HAVING IMPROVED VOLUNTARY ACCEPTANCE

CROSS-REFERENCE TO RELATED APPLICATIONS

This application is the National Stage entry of International Application No. PCT/EP2021/058295, filed 30 Mar. 2021, which claims priority to European Patent Application No. 20167444.7, filed 31 Mar. 2020.

BACKGROUND

Field

The present invention relates to the field of pharmaceutical compositions suitable for the oral administration of an active in animals. In particular, the present invention relates to a liquid drug-containing formulation comprising at least one drug, which is a hypoxia-inducible factor prolyl hydroxylase inhibitor and at least one natural oil of herbal origin. The present invention further relates to the use of a liquid formulation aid composition comprising at least one natural oil of herbal and/or animal origin in a liquid drug-containing formulation for improving the acceptance or voluntary acceptance of drug intake in animal.

Description of Related Art

Certain diseases require a daily and long-term medication in veterinary medicine, which usually need to be administered by untrained owners at home. Said medication is often to be administered orally, which is especially with cats and dogs difficult when the product has an undesired flavor. The animals tend to refuse the drug intake. This can be dangerous for the owners of the animal. Further, a complete drug intake of the needed medication cannot be ensured. These difficulties are even worse, if the medication needs to be administered daily over a prolonged administration period.

One example for the need of a daily long-term administration is the treatment and/or prophylaxis of diseases associated with hypoxia-inducible factor prolyl hydroxylase enzymes. Such diseases may be cardiovascular diseases, cardiac insufficiency, anemia, chronic kidney diseases, or renal insufficiency, especially anemia associated with chronic kidney disease. For example, WO2008/067871 describes certain substituted dihydroparazolones which are considered to have the aforementioned activities and WO2012/065967 describes a substituted sodium-1H-pyrazol-5-olate.

Most commercially available oral drug-containing formulations are aqueous based solutions or suspensions.

U.S. Pat. No. 5,756,474 relates to a non-aqueous oral-drench composition to treat parasitic diseases in mammals. It is disclosed that aqueous formulations generally have a better taste.

US20120141546 relates to an oil-based preparation for controlling parasitic protozoans and endoparasites in animals. The focus is on the single administration.

Hence, there is an ongoing need of a formulation for the oral medication for animals having a high acceptance or voluntary acceptance of the respective medicine to ensure the safety of the individual administering the drug-containing formulation and the compliance. In this connection, it has been an object of the present invention to provide a drug-containing formulation with a high acceptance or voluntary acceptance. Further, it has been an object of the present invention to provide a convenient drug administration for animals. In particular, it has been an object of the present invention to provide an improved intake of a drug-containing formulation comprising at least one hypoxia-inducible factor prolyl hydroxylase inhibitor. Further, it has been an object of the present invention to provide a liquid formulation aid composition to improve the drug intake in animal.

Further, it is desirable that the formulations show good bioavailability of the respective drug.

SUMMARY

It has surprisingly been found that at least one of these objects can be achieved by the liquid drug-containing formulation and/or the liquid formulation aid composition according to the present invention.

In a first aspect, the present invention relates to a liquid drug-containing formulation comprising the following components A) at least one drug, which is a hypoxia-inducible factor prolyl hydroxylase inhibitor,
B) at least one natural oil of herbal origin,
C) optionally at least one natural oil of animal origin, and
D) optionally at least one thickener.

DETAILED DESCRIPTION OF A PREFERRED EMBODIMENT

In the following, preferred embodiments of the components of the above formulation are described in further detail. It is to be understood that each preferred embodiment is relevant on its own as well as in combination with other preferred embodiments.

In a preferred embodiment A1 of the first aspect, the hypoxia-inducible factor prolyl hydroxylase inhibitor is a compound of formula (I)

(I)

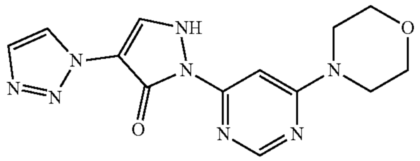

or a salt, stereoisomer, tautomer, or N-oxide thereof.

In a preferred embodiment A2 of the first aspect, the hypoxia-inducible factor prolyl hydroxylase inhibitor is a compound of formula (I), which is in the form of a salt having the formula (II)

(II)

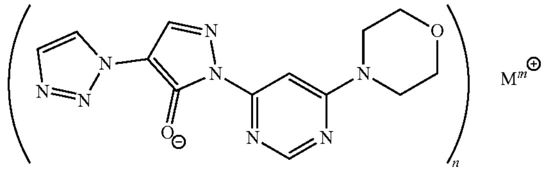

wherein

M is selected from the group consisting of lithium, sodium, potassium, calcium, magnesium, barium, manganese, copper, silver, zinc, iron, ammonium, and substituted ammonium in which one to four of the hydrogen atoms are replaced by $C_1$-$C_4$-alkyl, and preferably M is sodium;

m denotes the respective positive charge of the cation, being 1, 2, or 3, preferably 1; and n denotes the respective stoichiometric amount of the counter anion and is 1, 2, or 3, preferably 1; wherein n equals m so that the salt having the formula (II) is uncharged.

In a preferred embodiment A3 of the first aspect, the at least one natural oil of herbal origin is selected from the group consisting of almond oil, apricot kernel oil, canola oil, castor oil, coconut oil, cottonseed oil, flaxseed oil, grape oil, hemp oil, maize oil, olive oil, palm oil, peanut oil, sesame seed oil, soya oil, sunflower oil, thistle oil, rapeseed oil, rice bran oil, and wheat germ oil.

In a preferred embodiment A4 of the first aspect, the at least one natural oil of herbal origin is selected from the group consisting of modified almond oil, modified apricot kernel oil, modified canola oil, modified castor oil, modified coconut oil, modified cottonseed oil, modified flaxseed oil, modified grape oil, modified hemp oil, modified maize oil, modified olive oil, modified palm oil, modified peanut oil, modified sesame seed oil, modified soya oil, modified sunflower oil, modified thistle oil, modified rapeseed oil, modified rice bran oil, and modified wheat germ oil, wherein the modification is obtained by alcoholysis, preferably with glycerol, propylene glycol, or low molecular polyethylene glycol.

In a preferred embodiment A5 of the first aspect, the at least one natural oil of animal origin is present, which is selected from the group consisting of fish oil and salmon oil.

In a preferred embodiment A6 of the first aspect, the at least one natural oil of herbal origin is soya oil or sunflower oil and wherein at least one natural oil of animal origin is present, which is fish oil.

In a preferred embodiment A7 of the first aspect, the at least one natural oil of herbal origin is modified maize oil.

In a preferred embodiment A8 of the first aspect, the at least one thickener is present, which is a glycerol ester, and which is preferably is a glycerol ester with $C_{12}$-$C_{24}$ fatty acids and/or is a monoester, a diester, a triester, or a mixture thereof.

In a preferred embodiment A9 of the first aspect, the at least one thickener is present, which is glycerol dibehenate.

In a preferred embodiment A10 of the first aspect, the liquid drug-containing formulation as defined herein, further comprising the components E) at least one antioxidant selected from the group consisting of ascorbyl palmitate, butylhydroxytoluene, butylhydroxyanisole, citric acid, lecithins, propyl gallate, tocopherol, and combinations of these antioxidants; and/or F) at least one preservative selected from the group consisting of ethanol, propylene glycol, butanol, chlorobutanol, benzoic acid, sorbic acid, para-hydroxybenzoic esters, and combinations thereof; and/or G) optionally at least one surfactant.

In a preferred embodiment A11 of the first aspect, the liquid drug-containing formulation as defined herein comprises A) the hypoxia-inducible factor prolyl hydroxylase inhibitor in an amount of from 0.1 to 20 wt.-%, preferably from 0.5 to 10 wt.-%, based on the total weight of the liquid drug-containing formulation, B) the at least one natural oil of herbal origin in an amount of from 50 to 99.8 wt.-%, preferably from 70 to 98.97 wt.-%, based on the total weight of the liquid drug-containing formulation, C) optionally the at least one natural oil of animal origin in an amount of from 0.01 to 5 wt.-%, preferably from 0.01 to 1.5 wt.-%, based on the total weight of the liquid drug-containing formulation, D) optionally the at least one thickener in an amount of from 0.1 to 10 wt.-%, preferably from 0.5 to 5 wt.-%, based on the total weight of the liquid drug-containing formulation, E) optionally the at least one antioxidant in an amount of from 0.01 to 2 wt.-%, preferably from 0.01 to 1.5 wt.-%, based on the total weight of the liquid drug-containing formulation, and F) optionally the at least one preservative in an amount of from 0.01 to 2 wt.-%, preferably from 0.01 to 1.5 wt.-%, based on the total weight of the liquid drug-containing formulation.

In a second aspect, the present invention relates to the liquid drug-containing formulation as defined herein for use in the treatment and/or prophylaxis of diseases associated with hypoxia-inducible factor prolyl hydroxylase enzymes, wherein preferably said diseases are cardiovascular diseases, cardiac insufficiency, anemia, chronic kidney diseases, or renal insufficiency, in particular for use in the treatment of anemia associated with chronic kidney disease.

In a preferred embodiment B1 of the second aspect, the liquid drug-containing formulation can be administered for an administration period of at least two weeks without incurring problems with acceptance or voluntary acceptance.

In a preferred embodiment B2 of the second aspect, the liquid drug-containing formulation is administered to cats and dogs, preferably to cats.

In a third aspect, the present invention relates to the use of a liquid formulation aid composition comprising at least one natural oil of herbal and/or animal origin, preferably at least one natural oil of herbal origin, and optionally at least one thickener in a liquid drug-containing formulation for improving the acceptance or voluntary acceptance of drug intake in animal. Preferably, the present invention relates according to the third aspect, to the use of a liquid formulation aid composition comprising at least one natural oil of herbal origin and optionally at least one thickener in a liquid drug-containing formulation for improving the acceptance or voluntary acceptance of drug intake in animal.

In a preferred embodiment C1 of the third aspect, the liquid drug-containing formulation comprises the liquid formulation aid composition in an amount of at least 50 wt.-%, based on the total weight of a liquid drug-containing formulation.

In a preferred embodiment C2 of the third aspect, the acceptance or voluntary acceptance of drug intake is improved in cats and dogs, preferably in cats.

In a preferred embodiment C3 of the third aspect, the acceptance or voluntary acceptance of drug intake is improved over an administration period of at least two weeks.

In a preferred embodiment C4 of the third aspect, the at least one natural oil of herbal origin is comprised, which is selected from the group consisting of almond oil, apricot kernel oil, canola oil, castor oil, coconut oil, cottonseed oil, flaxseed oil, grape oil, hemp oil, maize oil, olive oil, palm oil, peanut oil, sesame seed oil, soya oil, sunflower oil, thistle oil, rapeseed oil, rice bran oil, and wheat germ oil, and is preferably soya oil or sunflower oil.

In a preferred embodiment C5 of the third aspect, the at least one natural oil of herbal origin is comprised, which is selected from the group consisting of modified almond oil, modified apricot kernel oil, modified canola oil, modified castor oil, modified coconut oil, modified cottonseed oil, modified flaxseed oil, modified grape oil, modified hemp oil, modified maize oil, modified olive oil, modified palm oil, modified peanut oil, modified sesame seed oil, modified soya oil, modified sunflower oil, modified thistle oil, modified rapeseed oil, modified rice bran oil, and modified wheat germ oil, and is preferably modified maize oil, wherein the modification is obtained by alcoholysis, preferably with glycerol, propylene glycol, or low molecular polyethylene glycol.

In a preferred embodiment C6 of the third aspect, the liquid formulation aid composition comprises the at least one natural oil of animal origin, which is preferably selected from the group consisting of fish oil and salmon oil, and is in particular fish oil.

In a preferred embodiment C7 of the third aspect, at least one thickener is present, which is a glycerol ester, which is preferably is a glycerol ester with $C_{12}$-$C_{24}$ fatty acids and/or is a monoester, a diester, a triester, or a mixture thereof.

In a preferred embodiment C8 of the third aspect, at least one thickener is present, which is glycerol dibehenate.

In a preferred embodiment C9 of the third aspect, the liquid formulation aid composition further comprises at least one antioxidant selected from the group consisting of ascorbyl palmitate, butylhydroxytoluene, butylhydroxyanisole, citric acid, lecithins, propyl gallate, tocopherol, and combinations of these antioxidants; and/or at least one preservative selected from the group consisting of ethanol, propylene glycol, butanol, chlorobutanol, benzoic acid, sorbic acid, para-hydroxybenzoic esters, and combinations thereof; and/or optionally at least one surfactant.

In a preferred embodiment C10 of the third aspect, the at least one natural oil of herbal origin is present in the liquid formulation aid composition in an amount of at least 90 wt.-%, based on the total weight of the liquid formulation aid composition.

DETAILED DESCRIPTION

Before describing in detail exemplary embodiments of the present invention, definitions important for understanding the present invention are given.

As used in this specification and in the appended claims, the singular forms of "a" and "an" also include the respective plurals unless the context clearly dictates otherwise. In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%. It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group, which preferably consists of these embodiments only. Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below. It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

The term "compounds of formula (I)" comprises the compound(s) as defined herein as well as a stereoisomer, salt, or tautomer thereof.

Depending on the substitution pattern, the compounds according to the invention may have one or more centers of chirality. The invention provides both the single pure enantiomers or pure diastereomers of the compounds according to the invention, and their mixtures and the use according to the invention of the pure enantiomers or pure diastereomers of the compounds according to the invention or their mixtures. Suitable compounds according to the invention also include all possible geometrical stereoisomers (cis/trans isomers or E/Z isomers) and mixtures thereof. Cis/trans isomers may e.g. be present with respect to an amide group. The term "stereoisomer(s)" encompasses both optical isomers, such as enantiomers or diastereomers, the latter existing due to more than one center of chirality in the molecule, as well as geometrical isomers (cis/trans isomers). The present invention relates to every possible stereoisomer of the compounds of formula (I), i.e. to single enantiomers or diastereomers, as well as to mixtures thereof.

Within the meaning of this invention, the terms "active", "active agent", "drug", and the like refer to any suitable active agent in any pharmaceutically acceptable chemical and morphological form and physical state.

The compounds of formula (I) may be amorphous or may exist in one or more different crystalline states (polymorphs) which may have different macroscopic properties such as stability or show different biological properties such as activities. The present invention relates to amorphous and crystalline compounds of formula (I), mixtures of different crystalline states of the respective compound of formula (I), as well as amorphous or crystalline salts thereof.

Salts of the compounds of the formula (I) may be pharmaceutically acceptable salts, such as those containing counterions present in drug products listed in the US FDA Orange Book database. They can be formed in a customary manner, e.g. by reacting the compound with an acid of the anion in question if the compound of formula (I) has a basic functionality, or by reacting acidic compounds according to the invention with a suitable base.

Suitable cationic counterions are in particular the ions of the alkali metals, preferably lithium, sodium and potassium, of the alkaline earth metals, preferably calcium, magnesium and barium, and of the transition metals, preferably aluminum, manganese, copper, silver, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, ($C_1$-$C_4$-alkoxy)-($C_1$-$C_4$-alkyl), hydroxy-($C_1$-$C_4$-alkoxy)-($C_1$-$C_4$-alkyl), phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy) ethyl-ammonium, bis(2-hydroxyethyl)ammonium, benzyltrimethylammonium and benzyltriethylammonium, furthermore the cations of 1,4-piperazine, meglumine, benzathine and lysine. Preferred cations are lithium, sodium, potassium, calcium, magnesium, barium, manganese, copper, silver, zinc, iron, ammonium, and substituted ammonium in which one to four of the hydrogen atoms are replaced by $C_1$-$C_4$-alkyl, in particular sodium.

Suitable anionic counterions are in particular chloride, bromide, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, trifluoroacetate, propionate and butyrate, furthermore lactate, gluconate, and the anions of poly acids such as succinate, oxalate, maleate, fumarate, malate, tartrate and citrate, furthermore sulfonate anions such as besylate (benzenesulfonate), tosylate (p-toluenesulfonate), napsylate (naphthalene-2-sulfonate), mesylate (methanesulfonate), esylate (ethanesulfonate), and ethanedisulfonate. They can be formed by reacting compounds according to the invention that have a basic functionality with an acid of the corresponding anion. Preferred salts of the compounds of formula (I) are chloride salts.

Tautomers may be formed, if a substituent is present at the compound of formula (I), which allows for the formation of tautomers such as keto-enol tautomers or the like.

The organic moieties mentioned in the above definitions of the variables are—like the term halogen—collective terms for individual listings of the individual group members. The prefix $C_n$-$C_m$ indicates in each case the possible number of carbon atoms in the group.

The term "alkyl" as used herein denotes in each case a straight-chain or branched alkyl group having usually from 1 to 4 carbon atoms, preferably from 1 to 3 carbon atoms. Examples of an alkyl group are methyl, ethyl, n-propyl, iso-propyl, n-butyl, 2-butyl, iso-butyl, and tert-butyl. Methyl, ethyl, n-propyl, iso-propyl, and iso-butyl, are particularly preferred.

As used in this specification and in the appended claims, the term "acceptance" refers to a "forced formulation intake" or "forced guided formulation intake" of an animal, wherein the formulation is administered directly into the animal's mouth. It is to be understood, that the formulation uptake is acceptable, if the animal is not reacting violently (e.g. biting) or adversely (e.g. convulsing).

As used in this specification and in the appended claims, the term "voluntary acceptance" refers to a voluntary oral formulation uptake of an animal. The formulation is administered into a bowl and the voluntary and autonomous uptake of the animal is evaluated over a maximum offering time of three minutes. In general, the procedure for evaluation of the voluntary acceptance in the animal can be assessed as follows:

A test item is offered daily in a food bowl for three minutes. The voluntary uptake of different formulations is assessed and recorded using a visual analogue scale (VAS), wherein 0 (cm) denotes worst possible voluntary intake and 10 (cm) denotes best possible voluntary intake.

| 0 (cm) | 10 (cm) |
|---|---|

In case of the worst possible intake (0 cm), the animal shows no interest and does not take up the test item. In case of the best possible intake (10 cm), the animal takes up the test item completely.

The assessor places a vertical mark on the line based on animal's behaviour (e.g. no uptake/shows interest, smells at the test item/partial consumption of the test formulation/looks for more). All voluntary intake assessments of one treatment day are done by the same individual.

Preferred embodiments regarding the liquid drug-containing formulation according to the present invention as well as the use of said liquid drug-containing formulation in the treatment and/or prophylaxis of diseases are described hereinafter. It is to be understood that the preferred embodiments of the invention are preferred alone or in combination with each other. Further, preferred embodiments regarding the use of the liquid formulation aid composition according to the present invention for improving the acceptance or voluntary acceptance of drug intake in animal are described hereinafter.

As indicated above, the present invention relates in one embodiment to a liquid drug-containing formulation comprising the following components A) at least one drug, which is a hypoxia-inducible factor prolyl hydroxylase inhibitor, B) at least one natural oil of herbal origin, C) optionally at least one natural oil of animal origin, and D) optionally at least one thickener.

Preferred embodiments regarding the components of the liquid drug-containing formulation, which are relevant for all aspects of the invention, are defined hereinafter.

According to the present invention, the liquid drug-containing formulation comprises at least one drug, which is a hypoxia-inducible factor prolyl hydroxylase inhibitor (also known as HIF-PHI). These inhibitors are members of a class of drugs that act by inhibiting prolyl hydroxylase which is responsible to break down the hypoxia-inducible factor (HIF) under normoxic conditions. These inhibitors are associated with diseases such as anemia, chronic kidney disease, and cancer. Examples for HIF prolyl hydroxylase inhibitors are daprodustat, molidustat, roxadustat, vadadustat, and desidustat. Hence, in one embodiment of the present invention, the hypoxia-inducible factor (HIF) prolyl hydroxylase inhibitor is selected from the group consisting of daprodustat, molidustat, roxadustat, vadadustat, and desidustat, and is in particular molidustat.

Preferably, the liquid drug-containing formulation according to the present invention, comprises the hypoxia-inducible factor prolyl hydroxylase inhibitor in an amount of from 0.1 to 20 wt.-%, more preferably from 0.5 to 10 wt.-%, even more preferably from 1 to 8 wt.-%, in particular from 1 to 5 wt.-%, based on the total weight of the liquid drug-containing formulation.

In one embodiment of the present invention, the HIF prolyl hydroxylase inhibitor is a compound of formula (I)

(I)

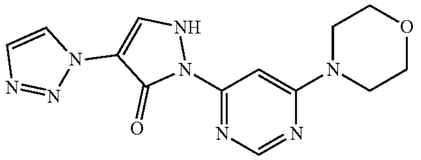

or a salt, stereoisomer, tautomer, or N-oxide thereof.

In one embodiment, the HIF prolyl hydroxylase inhibitor is a compound of formula (I) in the form of a salt having the formula (II)

(II)

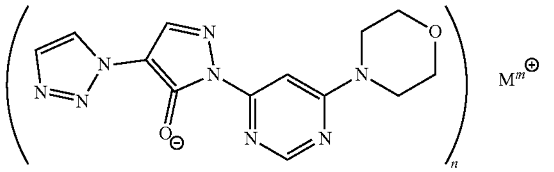

wherein

- M is selected from the group consisting of lithium, sodium, potassium, calcium, magnesium, barium, manganese, copper, silver, zinc, iron, ammonium, and substituted ammonium in which one to four of the hydrogen atoms are replaced by $C_1$-$C_4$-alkyl, and preferably M is sodium;
- m denotes the respective positive charge of the cation, being 1, 2, or 3, preferably 1; and
- n denotes the respective stoichiometric amount of the counter anion and is 1, 2, or 3, preferably 1; wherein n equals m so that the salt having the formula (II) is uncharged.

In a preferred embodiment of the present invention, the HIF prolyl hydroxylase inhibitor is in the form of the sodium salt of formula (IIa)

(IIa)

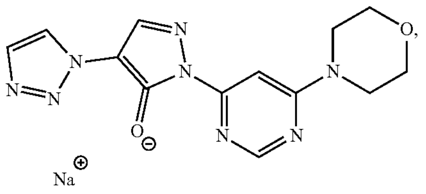

which is also known as sodium 1-[6-(morpholin-4-yl)pyrimidin-4-yl]-4-(1H-1,2,3-triazol-1-yl)-1H-pyrazol-5-olate.

In another preferred embodiment of the present invention, the HIF prolyl hydroxylase inhibitor is in the form of the potassium or ammonium salt of formula (II), which is also known as potassium 1-[6-(morpholin-4-yl)pyrimidin-4-yl]-4-(1H-1,2,3-triazol-1-yl)-1H-pyrazol-5-olate or ammonium 1-[6-(morpholin-4-yl)pyrimidin-4-yl]-4-(1H-1,2,3-triazol-1-yl)-1H-pyrazol-5-olate.

According to the present invention, the liquid drug-containing formulation comprises at least one natural oil of herbal origin. It is to be understood that according to the meaning of the present invention, the term "herbal" is interchangeable with "vegetable". Preferably, the liquid drug-containing formulation comprises the least one natural oil of herbal origin in an amount of at least 50 wt.-%, preferably from 50 to 99.8 wt.-%, more preferably from 70 to 98.97 wt.-%, even more preferably from 80 to 98.9 wt.-%, based on the total weight of the liquid drug-containing formulation.

In one embodiment of the present invention, the at least one natural oil of herbal origin is selected from the group consisting of almond oil, apricot kernel oil, canola oil, castor oil, coconut oil, cottonseed oil, flaxseed oil, grape oil, hemp oil, maize oil, olive oil, palm oil, peanut oil, sesame seed oil, soya oil, sunflower oil, thistle oil, rapeseed oil, rice bran oil, and wheat germ oil.

According to the present invention, the natural oils of herbal origin are obtained from natural products. According to the present invention, natural oils of herbal origin comprise at least 5 wt.-%, preferably at least 8 wt.-%, of unsaturated fatty acids, based on the total amount of fatty acids of said natural oils of herbal origin. In general, the natural oils of herbal origin may be obtained by mechanical expression or by extraction of the respective herbal (e.g. *Helianthus annuus* for sunflower oil), followed by an optional refining. Suitable antioxidants may be added.

In the following, exemplary descriptions of natural oils of herbal origin according to the present invention are given.

Maize oil, also known as corn oil, may be obtained from seeds of *Zea mays* L. by expression or by extraction followed by an optional refining. Preferably, the maize oil comprises 8.6 to 16.5 wt.-% of palmitic acid, up to 3.3 wt.-% of stearic acid, 20 to 42.2 wt.-% of oleic acid, 39.4 to 65.6 wt.-% of linoleic acid, 0.5 to 1.5 wt.-% of arachidic acid, up to 0.5 wt.-% of eicosenoic acid, and up to 0.5 wt.-% of behenic acid, based on the total amount of fatty acids.

Sunflower oil may be obtained from seeds of *Helianthus annuus* by mechanical expression or by extraction followed by an optional refining. Preferably, sunflower oil comprises 4 to 9 wt.-% of palmitic acid, 1 to 7 wt.-% of stearic acid, 14 to 40 wet.-% of oleic acid, and 48 to 74 wt.-% of linoleic acid, based on the total amount of fatty acids.

Thistle oil, also known as safflower oil, may be obtained from seeds of *Carthamus tinctorius* L. (type I) or from seeds of hybrids of *Carthamus tinctorius* L. (type II) by expression and/or extraction followed by an optional refining. Preferably, the thistle oil obtained from type I fraction comprises up to 0.2 wt.-% of saturated fatty acids of chain length less than C14, up to 0.2 wt.-% of myristic acid, 4 to 10 wt.-% of palmitic acid, 1 to 5 wt.-% of stearic acid, 8 to 21 wt.-% of oleic acid, 68 to 83 wt.-% of linoleic acid, up to 0.5 wt.-% of linolenic acid, up to 0.5 wt.-% of arachidic acid, up to 0.5 wt.-% of eicosenoic acid, and up to 1 wt.-% of behenic acid, based on the total amount of fatty acids. Preferably, the thistle oil obtained from type II fraction comprises up to 0.2 wt.-% of saturated fatty acids of chain length less than C14, up to 0.2 wt.-% of myristic acid, 3.6 to 6 wt.-% of palmitic acid, 1 to 5 wt.-% of stearic acid, 70 to 84 wt.-% of oleic acid, 7 to 23 wt.-% of linoleic acid, up to 0.5 wt.-% of linolenic acid, up to 1 wt.-% of arachidic acid, up to 1 wt.-% of eicosenoic acid, and up to 1.2 wt.-% of behenic acid, based on the total amount of fatty acids.

In general, it is to be understood that the natural oils of herbal origin according to the present invention may be obtained from the respective herbal by expression and/or extraction followed by an optional refining.

It is to be understood that according to the present invention, the natural oils of herbal origin may be any suitable natural oils of herbal origin known in the art as defined above and which may be obtained as described above. In one embodiment of the present invention, these natural oils of herbal origin may additionally be modified.

In one embodiment of the present invention, the at least one natural oil of herbal origin is selected from the group consisting of modified almond oil, modified apricot kernel oil, modified canola oil, modified castor oil, modified coconut oil, modified cottonseed oil, modified flaxseed oil, modified grape oil, modified hemp oil, modified maize oil, modified olive oil, modified palm oil, modified peanut oil, modified sesame seed oil, modified soya oil, modified sunflower oil, modified thistle oil, modified rapeseed oil, modified rice bran oil, and modified wheat germ oil, wherein the modification is obtained by alcoholysis, preferably with glycerol, propylene glycol, or low molecular polyethylene glycol. In this connection, it is to be understood that low molecular polyethylene glycol are defined as follows: $H—(O—CH_2—CH_2)_n—OH$, wherein n is selected from 1 to 5, preferably from 1 to 4, and in particular from 1 to 3 or from 1 to 2.

In general, the alcoholysis is an example of a solvolysis reaction, wherein the triglyceride reacts with an alcohol such as methanol or ethanol to give the methyl or ethyl esters of the fatty acid. In particular, glycerol may be used as alcohol. This reaction is also known as a transesterification reaction due to the exchange of the alcohol fragments.

The alcoholysis reaction is preferably followed by a winterization process to eliminate certain saturated mono-, di- and triglycerides.

Maisine® CC may be named as an exemplarily modified maize oil. It is obtained by alcoholysis of maize oil and a subsequent winterization of maize oil. The product comprises mono-, di-, and triglycerides, wherein the monoester fraction is comprised from 32 to 52 wt.-%, the diester fraction is comprised from 40 to 60 wt.-%, and the triester fraction is comprised from 5 to 20 wt.-%, based on the total amount of mono-, di-, and triglycerides.

In a particular embodiment of the present invention, the at least one natural oil of herbal origin is selected from the group consisting of sesame seed oil, soya oil, sunflower oil, thistle oil, and modified maize oil, wherein the modification is obtained by alcoholysis, preferably with glycerol, propylene glycol, or low molecular polyethylene glycol.

According to one particular embodiment the formulations or compositions described herein contain sunflower oil.

According to a further particular embodiment the formulations or compositions described herein contain soya oil.

According to a further particular embodiment the formulations or compositions described herein contain modified maize oil.

According to one embodiment of the present invention, the liquid drug-containing formulation comprises a mixture of modified and unmodified natural oils of herbal origin.

According to one embodiment of the present invention, the liquid drug-containing formulation further comprises at least one natural oil of animal origin. Preferably, the liquid drug-containing formulation comprises the at least one natural oil of animal origin from 0.01 to 5 wt.-%, more preferably from 0.01 to 2.5 wt.-%, even more preferably from 0.01 to 1.5 wt.-%, in particular from 0.01 to 1 wt.-%, based on the total weight of the liquid drug-containing formulation.

It is to be understood that according to the present invention, natural oils of animal origin may be any suitable natural oils of animal origin known in the art, e.g. fish oil, in particular cod-liver oil, and salmon oil. According to the present invention, natural oils of animal origin are obtained from natural products. In the following, exemplary descriptions of natural oils of animal origin according to the present invention are given.

Fish oil may be obtained from fish of families such as Engraulidae, Carangidae, Clupeidae, Osmeridae, Scombridae (except the genera *Thunnus* and *Sarda*), and Ammodytidae (type I), or from the genera *Thunnus* and *Sarda* with the family Scombridae (type II). The fish oil may comprise omega-3 acids such as alpha-linolenic acid (C18:3 n-3), moroctic acid (C18:4 n-3), eicosatetraenoic acid (C20:4 n-3), timnodonic (eicosapentaenoic) acid (C20:5 n-3; EPA), heneicosapentaenoic acid (C21:5 n-3), clupanodonic acid (C22:5 n-3), and cervonic (docosahexaenoic) acid (C22:6 n-3; DHA). Preferably, the fish oil obtained from type I comprises at least a total of omega-3 acids of 28 wt.-%, expressed as triglycerides. In particular, the fish oil obtained from type I comprises at least 13 wt.-% of EPA and at least 9 wt.-% of DHA, expressed as triglycerides. Preferably, the fish oil obtained from type II comprises at least a total of omega-3 acids of 28 wt.-%, expressed as triglycerides. In particular, the fish oil obtained from type II comprises 4 to 12 wt.-% of EPA and at least 20 wt.-% of DHA, expressed as triglycerides.

Cod-liver oil may be obtained from the fresh livers of cod, *Gadus morhua* L. and other species of Gadidae, wherein solid substances being removed by cooling and filtering. The cod-liver oil may comprise omega-3 acids such as alpha-linolenic acid (C18:3 n-3), moroctic acid (C18:4 n-3), eicosatetraenoic acid (C20:4 n-3), timnodonic (eicosapentaenoic) acid (C20:5 n-3; EPA), heneicosapentaenoic acid (C21:5 n-3), clupanodonic acid (C22:5 n-3), and cervonic (docosahexaenoic) acid (C22:6 n-3; DHA). Preferably, the cod-liver oil comprises EPA and DHA from 10 to 28 wt.-%, expressed as triglycerides. Cod-liver oil may further comprise 3 to 11 wt.-% of linoleic acid, based on the on the total amount of fatty acids.

Salmon oil may be obtained from Salmo salar. The positional distribution (β(2)-acyl) is 60 to 70% for cervonic (docosahexaenoic) acid (C22:6 n-3; DHA), 25 to 35% for timnodonic (eicosapentaenoic) acid (C20:5 n-3; EPA), and 40 to 55% for moroctic acid (C18:4 n-3). Preferably, the salmon oil comprises EPA and DHA from 10 to 28 wt.-%, expressed as triglycerides.

In one embodiment of the present invention, the at least one natural oil of animal origin is present, which is selected from the group consisting of fish oil and salmon oil.

In one embodiment of the present invention, the at least one natural oil of herbal origin is soya oil or sunflower oil and the at least one natural oil of animal origin is present, which is fish oil. In a preferred embodiment of the present invention, the at least one natural oil of herbal origin is sunflower oil and the at least one natural oil of animal origin is present, which is fish oil.

In another embodiment of the present invention, the at least one natural oil of herbal origin is modified maize oil and the at least one natural oil of animal origin is present, which is fish oil.

According to one embodiment of the present invention, the liquid drug-containing formulation further comprises at least one thickener. Preferably, the liquid drug-containing formulation as defined herein comprises the at least one thickener in an amount of from 0.1 to 10 wt.-%, preferably from 0.1 to 8 wt.-%, more preferably from 0.5 to 5 wt.-%, even more preferably from 0.5 to 2.5 wt.-%, based on the total weight of the liquid drug-containing formulation.

As suitable thickener cellulose derivatives such as methylcellulose, hydroxypropylcellulose, hydroxyethylcellulose, hydroxypropylmethylcellulose, carboxymethylcellulose, micro-crystalline cellulose; bentonites, kaolin, pectin, starches, modified starch, waxes, agar, paraffins, gelatin, alginates, polyvinylpyrrolidone, crospovidone, cetyl alcohol, stearates such as, for example, magnesium stearate, zinc stearate or glyceryl stearate, saturated or unsaturated long-chain fatty acids (C8-C24, high molecular weight polyethylene glycols (e.g. polyethylene glycol 2000), glycerol ester, and silicas may be mentioned.

In one embodiment of the present invention, the at least one thickener is a glycerol ester, and is preferably a glycerol ester with $C_{12}$-$C_{24}$ fatty acids and/or is a monoester, a diester, a triester, or a mixture thereof.

In a preferred embodiment of the present invention, the at least one thickener is glycerol dibehenate. Glycerol dibehenate may also be known under glyceryl dibehenate or glycerin dibehenate.

According to one embodiment of the present invention, the liquid drug-containing formulation further comprises the components E) at least one antioxidant; and/or F) at least one preservative; and/or G) optionally at least one surfactant.

Preferably, the liquid drug-containing formulation comprises the at least one antioxidant in an amount of from 0.01 to 2 wt.-%, preferably from 0.01 to 1.5 wt.-%, based on the total weight of the liquid drug-containing formulation and/or the at least one preservative in an amount of from 0.01 to 2 wt.-%, preferably from 0.01 to 1.5 wt.-%, based on the total weight of the liquid drug-containing formulation and/or the at least one surfactant in an amount of from 0.001 to 1 wt.-%, preferably from 0.01 to 0.3 wt.-%, based on the total weight of the liquid drug-containing formulation.

As suitable antioxidant ascorbyl palmitate, butylhydroxytoluene, butylhydroxyanisole, lecithins, sulfites (Na sulfite, Na metabisulfite), organic sulfides (cystine, cysteine, cysteamine, methionine, thioglycerol, thioglycolic acid, thiolactic acid), phenols (tocopherols, as well as vitamin E and vitamin E DPGS (d-alpha-tocopheryl polyethylene glycol 1000 succinate)), butylated hydroxyanisole, butylated hydroxytoluene, gallic acid (propyl, octyl, propyl gallate, and dodecyl gallate), organic acids (ascorbic acid, citric acid, tartaric acid, lactic acid) and salts and esters thereof may be mentioned. Preferably, antioxidants may be selected from the group consisting of ascorbyl palmitate, butylhydroxytoluene, butylhydroxyanisole, citric acid, lecithins, propyl gallate, and tocopherol.

As suitable preservative carboxylic acids (sorbic acid, propionic acid, benzoic acid, lactic acid), phenols (cresols, p-hydroxybenzoic esters such as methylparaben, propylparaben etc.), aliphatic alcohols (benzyl alcohol, ethanol, butanol etc.), quaternary ammonium compounds (benzalkonium chloride, cetylpyridinium chloride) may be mentioned. Preferably, preservatives may be selected from the group consisting of ethanol, propylene glycol, butanol, chlorobutanol, benzoic acid, sorbic acid, and para-hydroxybenzoic esters. In this connection, methyl 4-hydroxybenzoate, ethyl 4-hydroxybenzoate, and propyl 4-hydroxybenzoate may be named as preferred para-hydroxybenzoic esters.

Suitable surfactants are amphiphilic compounds. Mono-, di-, or tri-esters of sorbitan with fatty acids, polyoxyethylated compounds, such as polyoxyethylene sorbitan fatty acid esters, polyoxyethlyene castor oil derivatives, and poloxamers, and the like may be mentioned. Polyoxyethylated compounds, also referred to as polyethoxylated compounds, are prepared for example by reaction with ethylene oxide. They have one or more concatenated units of the formula $-[O-CH_2-CH_2]-$. Polyoxyethylated compounds which may be mentioned in particular are: nonionic amphiphilic polyoxyethylated compounds such as

- poloxamers, preferably with molar masses of from 100 to 5000 g/mol, particularly preferably with molar masses of from 1000 to 3500 g/mol. Poloxamer is the international non-proprietary name for block copolymers of ethylene oxide and methyloxirane,
- polyoxyethylene fatty acid glycerides, also called nonionic emulsifiers, preferably for example glycerol polyethylene glycol ricinoleate,
- polyoxyethylene sorbitan fatty acid esters, preferably for example polyoxyethylene 20 sorbitan monooleate,
- polyoxyethylene fatty acids such as macrogol 15 hydroxystearate (=Solutol HS15, obtainable by reacting 15 mol of ethylene oxide and 1 mol of 12-hydroxystearic acid)
- polyoxyethylene fatty alcohols such as hydroxypolyethoxydodecane.

Fatty acid or fatty alcohol stands in particular for the corresponding compounds having at least 6 carbon atoms and normally not more than 30 carbon atoms.

According to one embodiment of the present invention, the liquid drug-containing formulation further comprises the components E) at least one antioxidant selected from the group consisting of ascorbyl palmitate, butylhydroxytoluene, butylhydroxyanisole, citric acid, lecithins, propyl gallate, tocopherol, and combinations of these antioxidants; and/or F) at least one preservative selected from the group consisting of ethanol, propylene glycol, butanol, chlorobutanol, benzoic acid, sorbic acid, para-hydroxybenzoic esters, and combinations thereof; and/or G) optionally at least one surfactant.

According to one embodiment of the present invention, the liquid drug-containing formulation as defined herein comprises A) the hypoxia-inducible factor prolyl hydroxylase inhibitor in an amount of from 0.1 to 20 wt.-%, preferably from 0.5 to 10 wt.-%, based on the total weight of the liquid drug-containing formulation, B) the at least one natural oil of herbal origin in an amount of from 50 to 99.8 wt.-%, preferably from 70 to 98.97 wt.-%, based on the total weight of the liquid drug-containing formulation, C) optionally the at least one natural oil of animal origin in an amount of from 0.01 to 5 wt.-%, preferably from 0.01 to 1.5 wt.-%, based on the total weight of the liquid drug-containing formulation, D) optionally the at least one thickener in an amount of from 0.1 to 10 wt.-%, preferably from 0.5 to 5 wt.-%, based on the total weight of the liquid drug-containing formulation, E) optionally the at least one antioxidant in an amount of from 0.01 to 2 wt.-%, preferably from 0.01 to 1.5 wt.-%, based on the total weight of the liquid drug-containing formulation, and F) optionally the at least one preservative in an amount of from 0.01 to 2 wt.-%, preferably from 0.01 to 1.5 wt.-%, based on the total weight of the liquid drug-containing formulation.

According to one embodiment of the present invention, the liquid drug-containing formulation as defined herein does not comprise additional flavoring agents such as vanilla, anise, or honey flavor.

According to one embodiment of the present invention, the present invention relates to the liquid drug-containing formulation as defined herein for use in the treatment and/or prophylaxis of diseases associated with hypoxia-inducible factor prolyl hydroxylase enzymes, wherein preferably said diseases are cardiovascular diseases, cardiac insufficiency, anemia, chronic kidney diseases, or renal insufficiency, in particular for use in the treatment of anemia associated with chronic kidney disease.

According to one embodiment, the present invention relates to the liquid drug-containing formulation as defined herein for the control (or management) of secondary, non-regenerative anemia due to chronic kidney disease in animals, preferably in cats and dogs, in particular in cats.

According to one embodiment of the present invention, the liquid drug-containing formulation can be administered for an administration period of at least one week without incurring problems with acceptance or voluntary acceptance.

According to one embodiment of the present invention, the liquid drug-containing formulation can be administered for an administration period of at least two weeks without incurring problems with acceptance or voluntary acceptance.

According to one embodiment of the present invention, the liquid drug-containing formulation is administered to cats and dogs, preferably to cats.

According to one embodiment of the present invention, the liquid drug-containing formulation can be administered to cats for an administration period of at least two weeks without incurring problems with voluntary acceptance. According to a particular embodiment of the present invention, the liquid drug-containing formulation can be administered to cats for an administration period of at least four weeks without incurring problems with voluntary acceptance.

According to another embodiment of the present invention, the liquid drug-containing formulation can be administered to dogs for an administration period of at least two, in particular of at least four weeks without incurring problems with voluntary acceptance.

It is to be understood that according to the present invention, the liquid drug-containing formulation as defined herein is administered orally to the animal.

According to the present invention, the voluntary acceptance of a liquid drug-containing formulation according to the invention is at least 7, preferably at least 8, determined as defined herein.

As indicated above, the present invention further relates to the use of a liquid formulation aid composition comprising at least one natural oil of herbal origin for improving the acceptance or voluntary acceptance of drug intake.

As indicated above, the present invention further relates to the use of a liquid formulation aid composition comprising at least one natural oil of animal origin for improving the acceptance or voluntary acceptance of drug intake.

In one embodiment of the present invention, the liquid formulation aid composition comprises at least one natural oil of herbal origin and at least one natural oil of animal origin.

In one embodiment of the present invention, the liquid drug-containing formulation comprises the liquid formulation aid composition in an amount of at least 20 wt.-%, preferably at least 40 wt.-%, more preferably at least 50 wt.-%, even more preferably at least 70 wt.-%, in particular at least 80 wt.-%, based on the total weight of the liquid drug-containing formulation.

In one embodiment of the present invention, the acceptance or voluntary acceptance of drug intake is improved in cats and dogs, preferably in cats.

In one embodiment of the present invention, the acceptance or voluntary acceptance of drug intake is improved over an administration period of at least one week.

In one embodiment of the present invention, the acceptance or voluntary acceptance of drug intake is improved over an administration period of at least two weeks.

In a particular embodiment of the present invention, the acceptance or voluntary acceptance of drug intake is improved over an administration period of at least four weeks.

It is to be understood that the at least one natural oil of herbal origin which is comprised in the liquid formulation aid composition is defined as outlined in more detail above.

In one embodiment of the present invention, the at least one natural oil of herbal origin is comprised, which is selected from the group consisting of almond oil, apricot kernel oil, canola oil, castor oil, coconut oil, cottonseed oil, flaxseed oil, grape oil, hemp oil, maize oil, olive oil, palm oil, peanut oil, sesame seed oil, soya oil, sunflower oil, thistle oil, rapeseed oil, rice bran oil, and wheat germ oil, and is preferably soya oil or sunflower oil.

It is to be understood that according to the present invention, the natural oils of herbal origin which is comprised in the liquid formulation aid composition may be any suitable natural oils of herbal origin known in the art as defined above and which may be obtained as described above. These natural oils of herbal origin may additionally be modified.

In another embodiment of the present invention, the at least one natural oil of herbal origin is comprised, which is selected from the group consisting of modified almond oil, modified apricot kernel oil, modified canola oil, modified castor oil, modified coconut oil, modified cottonseed oil, modified flaxseed oil, modified grape oil, modified hemp oil, modified maize oil, modified olive oil, modified palm oil, modified peanut oil, modified sesame seed oil, modified soya oil, modified sunflower oil, modified thistle oil, modified rapeseed oil, modified rice bran oil, and modified wheat germ oil, and is preferably modified maize oil, wherein the modification is obtained by alcoholysis, preferably with glycerol, propylene glycol, or low molecular polyethylene glycol.

In a particular embodiment of the present invention, the at least one natural oil of herbal origin is comprised, which is selected from the group consisting of sesame seed oil, soya oil, sunflower oil, thistle oil, and modified maize oil, wherein the modification is obtained by alcoholysis, preferably with glycerol, propylene glycol, or low molecular polyethylene glycol.

In one embodiment of the present invention, the liquid formulation aid composition comprises the at least one natural oil of animal origin, which is preferably selected from the group consisting of fish oil and salmon oil, and is in particular fish oil.

In one embodiment of the present invention, at least one thickener is present, preferably in the liquid formulation aid composition, which is a glycerol ester, which is preferably is a glycerol ester with $C_{12}$-$C_{24}$ fatty acids and/or is a monoester, a diester, a triester, or a mixture thereof.

In one embodiment of the present invention, at least one thickener is present, preferably in the liquid formulation aid composition, which is glycerol dibehenate.

In one embodiment of the present invention, the liquid formulation aid composition further comprises at least one antioxidant selected from the group consisting of ascorbyl palmitate, butylhydroxytoluene, butylhydroxyanisole, citric acid, lecithins, propyl gallate, tocopherol, and combinations of these antioxidants; and/or at least one preservative selected from the group consisting of ethanol, propylene glycol, butanol, chlorobutanol, benzoic acid, sorbic acid, para-hydroxybenzoic esters, and combinations thereof; and/or optionally at least one surfactant.

In one embodiment of the present invention, the at least one natural oil of herbal origin is present in the liquid formulation aid composition in an amount of at least 50 wt.-%, preferably at least 70 wt.-%, more preferably at least 90 wt.-%, even more preferably at least 93 wt.-%, in particular at least 95 wt.-%, based on the total weight of the liquid formulation aid composition.

In another embodiment of the present invention, the at least one natural oil of animal origin is present in the liquid formulation aid composition in an amount of at least 50 wt.-%, preferably at least 70 wt.-%, more preferably at least 90 wt.-%, even more preferably at least 93 wt.-%, in particular at least 95 wt.-%, based on the total weight of the liquid formulation aid composition.

It is further to be understood that, the at least one natural oil of animal origin, the at least one thickener, the at least one antioxidant, the at least one preservative, and the at least one surfactant which may be comprised in the liquid formulation aid composition are defined as outlined in more detail above.

According to one embodiment of the present invention, the liquid formulation aid composition as defined herein does not comprise additional flavoring agents such as vanilla, anise, or honey flavor.

According to the present invention, the liquid formulation aid composition improves the voluntary acceptance of the liquid drug-containing formulation in that it is at least 7, preferably at least 8, determined as defined herein.

The present invention is further illustrated by the following examples.

Used Material

Compritol® 888ATO was purchased from Gattefosse and is a glyceryl dibehenate. It is obtained by esterification of glycerol with behenic acid (C22 fatty acids), followed by atomization. The product comprises mono-, di-, and triglycerides of behenic acid, wherein the diester fraction is comprised from 40 to 60 wt.-%.

Maisine® CC was purchased from Gattefosse and is a modified maize oil. It is obtained by alcoholysis of maize oil and a subsequent winterization. The product comprises mono-, di-, and triglycerides, wherein the monoester fraction is comprised from 32 to 52 wt.-%, the diester fraction is comprised from 40 to 60 wt.-%, and the triester fraction is comprised from 5 to 20 wt.-%.

More specifically Maisine® CC consists of mono-, di- and triglycerides of mainly linoleic (C18:2) and oleic (C18:1) acids, the diester fraction being predominant.

Maisine® CC is also known as corn oil mono-, di- and triglycerides, glycerol/glyceryl monolinoleate (EP, USP-NF) or corn glycerides (FDA IID).

Miglyol® 810 was purchased from IOI Oleo GmbH and is a mixture of decanoyl- and octanoyl glycerides. It is also known as Caprylic/Capric Triglyceride or Triglycerides, medium chain.

Miglyol® 812 was purchased from IOI Oleo GmbH and is a mixture of decanoyl- and octanoyl glycerides. It is also known as Caprylic/Capric Triglyceride or Triglycerides, medium chain.

Miglyol® 840 was purchased from IOI Oleo GmbH and is a mixture of glycol mono- and diesters of caprylic acid (C8H16O2) and capric acid (C10H$_2$OO2), wherein the diesters fraction is predominant.

Solbrol P was purchased from Fluka.

Solbrol M was purchased from Fluka.

Tween 20 was purchased from Croda GmbH.

Tween 80 was purchased from Croda GmbH.

Avicel CL 611 was purchased from FMC Corporation.

The natural oils of herbal an animal origin were purchased from Fluka.

Compound A can be accessed according to the synthesis disclosed in e.g. WO2013167552A1 and is sodium 1-[6-(morpholin-4-yl)pyrimidin-4-yl]-4-(1H-1,2,3-triazol-1-yl)-1H-pyrazol-5-olate having formula (IIa)

(IIa)

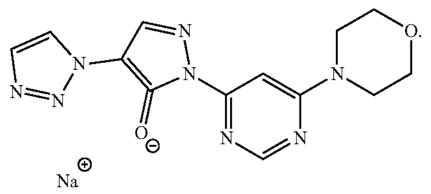

In the following, the general procedure for evaluation of the voluntary acceptance in cats will be described.

A test item was offered daily in a food bowl for three minutes. The voluntary uptake of different formulations were assessed and recorded using a visual analogue scale (VAS), wherein 0 (cm) denotes worst possible voluntary intake and 10 (cm) denotes best possible voluntary intake.

| 0 (cm) | 10 (cm) |
|---|---|

In case of the worst possible intake (0 cm), the cat showed no interest and did not take up the test item. In case of the best possible intake (10 cm), the cat took up the test item completely.

The assessor placed a vertical mark on the line based on cat's behaviour (e.g. no uptake/shows interest, smells at the test item/partial consumption of the test formulation/looks for more). All voluntary intake assessments of one treatment day were done by the same individual.

Example 1

In the following, the voluntary acceptance of several natural oils of herbal origin and of animal origin (Ex. 1.1 to 1.8) were tested. Additionally, the voluntary acceptance of a mixture comprising a natural oil of herbal origin and a triglyceride (Ex. 1.9) was tested.

For the voluntary acceptance test, eight cats were tested following the above-mentioned general procedure for evaluation over a time period of four or seven days (compare Table 1.a and 1.b). The cats were offered 0.5 ml of the respective oil.

The respective results were obtained via the following exemplarily set up. The mean values are depicted in Tables 1.a and 1.b and the more detailed results are depicted in Table 1.c.

Two test groups comprising each eight cats were applied. Within one voluntary acceptance test phase (seven days), only one formulation was tested.

To accustom the cats to the procedure of licking fluids from a bowl, the cats were offered water and/or milk per animal for the duration of three days, providing a baseline phase value. Following to the baseline phase, the respective natural oils of herbal or animal origin or the mixture comprising a natural oil of herbal origin and triglycerides were offered.

Test group 1 (cats 1 to 9) had been offered the natural oils of herbal origin according to Ex. 1.1, 1.2, 1.3, 1.6, and 1.7.

Test group 2 (cats 10 to 17) had been offered the natural oils of herbal or animal origin or a mixture comprising a natural oil of herbal origin and a triglyceride according to Ex. 1.4, 1.5, 1.8, and 1.9.

The detailed voluntary acceptance results are depicted in Table 1.c.

Preparation of the mixture comprising sunflower oil and triglyceride according to Ex. 1.9:

Sunflower oil was placed in a flask. Miglyol 810 and Miglyol 812 were added under stirring and the mixture was stirred for further 10 minutes.

TABLE 1a

Natural oils of herbal origin according to Ex. 1.1 to 1.5 and the test results. The solids %-value refers to the amounts (Amt) in % by weight.

| Ingredient (Trade Name) | Ex. 1.1 Solids [%] | Ex. 1.2 Solids [%] | Ex. 1.3 Solids [%] | Ex. 1.4 Solids [%] | Ex. 1.5 Solids [%] |
|---|---|---|---|---|---|
| Soya oil | 100 | 100 | — | — | — |
| Maize oil | — | — | 100 | — | — |
| Thistle oil | — | — | — | 100 | — |
| Sesame oil | — | — | — | — | 100 |
| No. of cats tested | 7 | 1 | 8 | 8 | 8 |
| Administration period [1/d] | 7 | 4 | 7 | 7 | 7 |
| Voluntary acceptance [mean] | 8.7 | 10.0 | 7.9 | 8.1 | 8.4 |

TABLE 1b

Natural oils of herbal origin and of animal origin according to Ex. 1.6 to 1.8 and the mixture comprising sunflower oil and triglyceride according to Ex. 1.9 and the test results. The solids %-value refers to the amounts (Amt) in % by weight.

| | Ex. 1.6 | Ex. 1.7 | Ex. 1.8 | Ex. 1.9 | |
|---|---|---|---|---|---|
| Ingredient (Trade Name) | Solids [%] | Solids [%] | Solids [%] | Amt [g] | Solids [%] |
| Sunflower oil | 100 | — | — | 60 | 50 |
| Salmon oil | — | 100 | — | — | — |
| Modified maize oil | — | — | 100 | — | — |
| Triglyceride (Miglyol 810) | — | — | — | 30 | 25 |
| Triglyceride (Miglyol 812) | — | — | — | 30 | 25 |
| No. of cats tested | 8 | 8 | 8 | 8 | |
| Administration period [1/d] | 7 | 7 | 7 | 7 | |
| Voluntary acceptance [mean] | 8.8 | 7.9 | 8.9 | 8.3 | |

TABLE 1.c

Detailed voluntary acceptance test results for the natural oils of herbal origin and of animal origin according to Ex. 1.1 to 1.8 and the mixture of sunflower oil with triglyceride according to Ex. 1.9. Baseline is abbreviated with Bl..

| | cats | | | | | | | | | |
|---|---|---|---|---|---|---|---|---|---|---|
| Ex. | 1 | 2 | 3 | 4 | 5 | 6 | 7 | 8 | 9 | mean |
| Bl. | 10.0 | 10.0 | 10.0 | 10.0 | 10.0 | 10.0 | 10.0 | 10.0 | 10.0 | 10.0 |
| 1.1 & 1.2 | 10.0 | 10.0 | — | 3.9 | 8.6 | 10.0 | 9.9 | 10.0 | 8.9 | 8.9 |
| 1.3 | 10.0 | 10.0 | — | 4.3 | 10.0 | 9.7 | 9.0 | 10.0 | 0.0 | 7.9 |
| 1.6 | 10.0 | — | 8.1 | 1.9 | 10.0 | 10.0 | 10.0 | 10.0 | 10.0 | 8.8 |
| 1.8 | 10.0 | — | 6.1 | 6.0 | 9.4 | 10.0 | 10.0 | 10.0 | 10.0 | 8.9 |

| | cats | | | | | | | | |
|---|---|---|---|---|---|---|---|---|---|
| Ex. | 10 | 11 | 12 | 13 | 14 | 15 | 16 | 17 | |
| Bl. | 10.0 | 10.0 | 10.0 | 10.0 | 10.0 | 10.0 | 10.0 | 10.0 | 10.0 |
| 1.4 | 8.6 | 4.4 | 7.7 | 10.0 | 9.3 | 5.6 | 10.0 | 9.1 | 8.1 |
| 1.5 | 6.6 | 4.3 | 9.9 | 10.0 | 10.0 | 6.6 | 10.0 | 9.9 | 8.4 |

TABLE 1.c-continued

Detailed voluntary acceptance test results for the natural oils of herbal origin and of animal origin according to Ex. 1.1 to 1.8 and the mixture of sunflower oil with triglyceride according to Ex. 1.9. Baseline is abbreviated with Bl..

| | | | | | | | | | |
|---|---|---|---|---|---|---|---|---|---|
| 1.7 | 9.9 | 10.0 | 10.0 | 10.0 | 0.9 | 9.4 | 3.3 | 10.0 | 7.9 |
| 1.9 | 8.6 | 4.1 | 10.0 | 10.0 | 10.0 | 3.3 | 10.0 | 10.0 | 8.3 |

Best voluntary acceptance is shown by sunflower oil, soya oil, and modified maize oil.

Example 2

In the following, the voluntary acceptance of the liquid placebo formulations according to Ex. 2.1 to 2.4 were tested.

For the voluntary acceptance test, eight cats were tested following the above mentioned general procedure for evaluation over a time period of 8, 23, or 28 days (compare Table 2.a and 2.b). In this connection, it should be noted that the evaluation of the formulation according to Ex. 2.4 was stopped after eight days, due to the poor uptake. 0.2 ml/kg bw (body weight of cat) of the liquid placebo formulation was offered.

The respective results were obtained via the following exemplarily set up. The mean values are depicted in Tables 2.a and 2.b and the more detailed results for Ex. 2.1 to 2.4 are depicted in Table 2.c.

Two test groups comprising each eight cats were applied. Within one voluntary acceptance test phase (23 or 28 days), only one formulation was tested.

To accustom the cats to the procedure of licking fluids from a bowl, the cats were offered water and/or milk per animal for the duration of four days, providing a baseline phase value. Following to the baseline phase, the respective liquid placebo formulation was tested.

Test group 1 (cats 18 to 25) had been offered the liquid placebo formulation Ex. 2.1 and Ex. 2.2.

Test group 2 (cats 26 to 33) had been offered the liquid placebo formulation Ex. 2.3 and Ex. 2.4.

The detailed voluntary acceptance results are depicted in Table 2.c.

Preparation of the liquid placebo formulations according to Ex. 2.1 to 2.4:

Ex. 2.1 and 2.2: Sunflower oil was placed in a flask. Fish oil was added and the mixture was heated to 70° C. Butylhydroxytoluene, sorbic acid, and Compritol were added under stirring and the mixture was stirred for further 10 minutes before the mixture was let cooled to room temperature.

Ex. 2.3: Miglyol was placed in a flask and heated to 75° C. Butylhydroxytoluene, sorbic acid, and Compritol were added under stirring and the mixture was stirred for further 10 minutes before the mixture was let cooled to room temperature.

Ex. 2.4: Water was placed in a flak. Sodium citrate was added to obtain a pH of 8.37, citric acid was added to obtain a pH of 6.03, Solbrol M, and Solbrol P were added under stirring and the mixture was heated to 40° C. and stirred until the parabens were dissolved before the mixture was let cooled to room temperature. Sorbitol, propylene glycol, vanilla flavor, Tween 20, Tween 80, and Avicel were added under stirring. The final citric acid was added to obtain a pH of 5.52 and the mixture was stirred for further 10 minutes.

TABLE 2.a

Liquid placebo formulations according to Ex. 2.1 and 2.2 and the test results. The solids %-value refers to the amounts (Amt) in % by weight.

| | Ex. 2.1 | | Ex. 2.2 | |
|---|---|---|---|---|
| Ingredient (Trade Name) | Amt [g] | Solids [%] | Amt [g] | Solids [%] |
| Sunflower oil | 452.0 | 98.6 | 452.0 | 98.6 |
| Fish oil | 0.5 | 0.1 | 0.5 | 0.1 |
| Sorbic acid | 0.4 | 0.09 | 0.4 | 0.09 |
| Butylhydroxytoluene (BHT) | 0.6 | 0.1 | 0.6 | 0.1 |
| Glyceryl Dibehenate (Compritol 888 ATO) | 5 | 1.1 | 5 | 1.1 |
| Total | 458.50 | 100 | 458.50 | 100 |
| No. of cats tested | 7 | | 1 | |
| Administration period [1/d] | 28 | | 23 | |
| Voluntary acceptance [mean] | 9.2 | | 9.7 | |

TABLE 2.b

Liquid placebo formulations according to Ex. 2.3 and 2.4 and the test results. The solids %-value refers to the amounts (Amt) in % by weight.

| | Ex. 2.3 | | Ex. 2.4 | |
|---|---|---|---|---|
| Ingredient (Trade Name) | Amt [g] | Solids [%] | Amt [g] | Solids [%] |
| Triglyceride (Miglyol 840) | 452.4 | 97.6 | — | — |
| Sorbic acid | 0.4 | 0.09 | — | — |

TABLE 2.b-continued

Liquid placebo formulations according to Ex. 2.3 and 2.4 and the test results. The solids %-value refers to the amounts (Amt) in % by weight.

| | Ex. 2.3 | | Ex. 2.4 | |
|---|---|---|---|---|
| Ingredient (Trade Name) | Amt [g] | Solids [%] | Amt [g] | Solids [%] |
| Butylhydroxytoluene (BHT) | 0.5 | 0.1 | — | — |
| Glyceryl Dibehenate (Compritol 888 ATO) | 10 | 2.2 | — | — |
| Aqua bidest. | — | — | 411.9 | 77.4 |
| Sodium citrate | — | — | 1.3 | 0.2 |
| Citric acid | — | — | 7.6 | 1.4 |
| Propylparaben (Solbrol P) | — | — | 0.1 | 0.02 |
| Methylparaben (Solbrol M) | — | — | 0.9 | 0.2 |
| Sorbitol | — | — | 50 | 9.4 |
| Propylene glycol | — | — | 50 | 9.4 |
| Vanilla flavor | — | — | 1 | 0.2 |
| Polysorbate 20 (Tween 20) | — | — | 0.8 | 0.2 |
| Polysorbate 80 (Tween 80) | — | — | 0.8 | 0.2 |
| Mixture of cellulose and carboxy methyl cellulose (Avicel CL 611) | — | — | 8 | 1.5 |
| Total | 463.3 | 100 | 458.51 | 100 |
| No. of cats tested | 8 | | 8 | |
| Administration period [1/d] | 28 | | 8 | |
| Voluntary acceptance [mean] | 6.5 | | 0.3 | |

TABLE 2.c

Detailed voluntary acceptance test results for the liquid placebo formulations according to Ex. 2.1 to 2.4.

| | cats | | | | | | | | |
|---|---|---|---|---|---|---|---|---|---|
| Formulation | 18 | 19 | 20 | 21 | 22 | 23 | 24 | 25 | mean |
| Baseline | 9.6 | 9.5 | 8.8 | 9.5 | 9.9 | 8.3 | 9.4 | 10.0 | 9.4 |
| Oily (Ex. 2.1 & 2.2) | 9.9 | 9.8 | 9.1 | 9.8 | 10.0 | 8.4 | 9.7 | 7.3 | 9.3 |
| | cats | | | | | | | | |
| | 26 | 27 | 28 | 29 | 30 | 31 | 32 | 33 | |
| Baseline | 9.0 | 7.9 | 8.5 | 8.3 | 6.4 | 9.6 | 10.0 | 8.0 | 8.5 |
| Watery (Ex. 2.4) | 0.0 | 0.0 | 0.0 | 0.0 | 0.0 | 0.3 | 0.9 | 1.6 | 0.3 |
| Baseline | 10.0 | 9.5 | 10.0 | 10.0 | 9.3 | 10.0 | 10.0 | 10.0 | 9.8 |
| Miglyol (Ex. 2.3) | 4.1 | 2.8 | 6.8 | 7.3 | 3.2 | 7.6 | 10.0 | 9.9 | 6.5 |

Best voluntary acceptance is shown by liquid placebo formulations comprising sunflower oil.

Example 3

In the following, the voluntary acceptance of the liquid drug-containing formulations 3.1 to 3.6 was tested.

For the voluntary acceptance test, eight cats were tested following the above mentioned general procedure for evaluation over a time period of three or seven days. 0.2 ml/kg bw (body weight of cat) of the liquid drug-containing formulation was offered. Due to animal welfare, the healthy cats had not been offered the liquid drug-containing formulations over a time period of 28 days.

The respective results were obtained via the following exemplarily set up. The mean values are depicted in Tables 3.a and 3.b and the more detailed results for Ex. 3.1 and 3.2 are depicted in Table 3.c.

Two test groups comprising each eight cats were applied. Within one voluntary acceptance test phase (three or seven days), only one formulation was tested.

To accustom the cats to the procedure of licking fluids from a bowl, the cats were offered water and/or milk per animal for the duration of four days, providing a baseline phase value. Following to the baseline phase, the respective liquid drug-containing formulation was tested.

Test group 1 (cats 18 to 25) had been offered the liquid drug-containing formulation Ex. 3.1.

Test group 2 (cats 26 to 33) had been offered the liquid drug-containing formulation Ex. 3.2.

The detailed voluntary acceptance results are depicted in Table 3.c.

The results for the liquid drug-containing formulation according to Ex. 3.3 to Ex. 3.6 were achieved accordingly.

Preparation of the liquid drug-containing formulations according to Ex. 3.1 to 3.6:

Ex. 3.1 and 3.4: Sunflower oil was placed in a flask. Fish oil was added and the mixture was heated to 70° C. (Ex. 3.1) and 75° C. (Ex. 3.4), respectively. Butylhydroxytoluene, sorbic acid, and Compritol were added under stirring and the mixture was stirred for further 10 minutes before the mixture was let cooled to room temperature. Compound A was added under stirring and the mixture was stirred for further 10 minutes.

Ex. 3.2: Water was placed in a flak. Sodium citrate was added to obtain a pH of 8.27, citric acid was added to obtain a pH of 6.01, Solbrol M, and Solbrol P were added under stirring and the mixture was heated to 40° C. and stirred until the parabens were dissolved before the mixture was let cooled to room temperature. Sorbitol, propylene glycol, vanilla flavor, Tween 20, Tween 80, and Avicel were added under stirring. Citric acid was added to obtain a pH of 5.50 and Compound A was added. The final citric acid was added to obtain a pH of 5.5.0 again and the mixture was stirred for further 10 minutes.

Ex. 3.3: Sunflower oil was placed in a flask and heated to 75° C. Sorbic acid, butylhydroxytoluene, and Compritol were added under stirring. The mixture was let cooled to room temperature before Compound A was added and stirred further 10 minutes.

Ex. 3.5: Miglyol 840 was placed in a flask and heated to 75° C. Sorbic acid, butylhydroxytoluene, and Compritol were added under stirring. The mixture was let cooled to room temperature and Compound A was added under stirring and the mixture was stirred for further 10 minutes.

Ex. 3.6: Miglyol 840 was placed in a flask. Fish oil was added and the mixture was heated to 75° C. Sorbic acid, butylhydroxytoluene, and Compritol were added under stirring. The mixture was let cooled to room temperature and Compound A was added under stirring and the mixture was stirred for further 10 minutes.

TABLE 3.a

Liquid drug-containing formulations according to Ex. 3.1 to 3.3 and the test results. The solids %-value refers to the amounts (Amt) in % by weight.

| Ingredient (Trade Name) | Ex. 3.1 Amt [g] | Ex. 3.1 Solids [%] | Ex. 3.2 Amt [g] | Ex. 3.2 Solids [%] | Ex. 3.3 Amt [g] | Ex. 3.3 Solids [%] |
|---|---|---|---|---|---|---|
| Sunflower oil | 222.7 | 95.9 | — | — | 91.3 | 95.1 |
| Fish oil | 0.3 | 0.1 | — | — | — | — |
| Sorbic acid | 0.2 | 0.09 | — | — | 0.08 | 0.08 |
| Butylhydroxytoluene (BHT) | 0.3 | 0.1 | — | — | 0.1 | 0.1 |
| Glyceryl Dibehenate (Compritol 888 ATO) | 2.5 | 1.1 | — | — | 2 | 2.1 |
| Compound A | 6.3 | 2.7 | 6.3 | 2.3 | 2.5 | 2.6 |
| Aqua bidest. | — | — | 182.2 | 65.6 | — | — |
| Sodium citrate | — | — | 0.6 | 0.2 | — | — |
| Citric acid | — | — | 32.6 | 11.7 | — | — |
| Propylparaben (Solbrol P) | — | — | 0.05 | 0.02 | — | — |
| Methylparaben (Solbrol M) | — | — | 0.5 | 0.2 | — | — |
| Sorbitol | — | — | 25 | 9 | — | — |
| Propylene glycol | — | — | 25 | 9 | — | — |
| Vanilla flavor | — | — | 0.5 | 0.2 | — | — |
| Polysorbate 20 (Tween 20) | — | — | 0.4 | 0.14 | — | — |
| Polysorbate 80 (Tween 80) | — | — | 0.4 | 0.14 | — | — |
| Mixture of cellulose and carboxy methyl cellulose (Avicel CL 611) | — | — | 4 | 1.4 | — | — |
| Total | 232.3 | 100 | 277.6 | 100 | 96 | 99.9 |
| No. of cats tested | 8 | | 8 | | 12 | |
| Administration period [1/d] | 7 | | 7 | | 3 | |
| Voluntary acceptance [mean] | 8.8 | | 0.1 | | 8.4 | |

TABLE 3.b

Liquid drug-containing formulations according to Ex. 3.3 to 3.6 and the test results. The solids %-value refers to the amounts (Amt) in % by weight.

| Ingredient (Trade Name) | Ex. 3.4 Amt [g] | Ex. 3.4 Solids [%] | Ex. 3.5 Amt [g] | Ex. 3.5 Solids [%] | Ex. 3.6 Amt [g] | Ex. 3.6 Solids [%] |
|---|---|---|---|---|---|---|
| Sunflower oil | 91.3 | 95.1 | — | — | — | — |
| Fish oil | 0.1 | 0.1 | — | — | 0.1 | 0.1 |
| Sorbic acid | 0.08 | 0.08 | 0.08 | 0.08 | 0.08 | 0.08 |
| Butylhydroxytoluene (BHT) | 0.1 | 0.1 | 0.1 | 0.1 | 0.1 | 0.1 |
| Glyceryl Dibehenate (Compritol 888 ATO) | 2 | 2.1 | 2 | 2.1 | 2 | 2.1 |
| Compound A | 2.5 | 2.6 | 2.5 | 2.6 | 2.5 | 2.6 |
| Triglyceride (Miglyol 840) | — | — | 90.4 | 95.1 | 90 | 95 |
| Total | 96 | 100 | 95.1 | 100 | 94.8 | 100 |
| No. of cats tested | 12 | | 12 | | 12 | |
| Administration period [1/d] | 3 | | 3 | | 3 | |
| Voluntary acceptance [mean] | 8.2 | | 7.8 | | 7.7 | |

TABLE 3.c

Detailed voluntary acceptance test results for the liquid drug-containing formulations according to Ex. 3.1 and 3.2.

| Suspension | cats 21 | 18 | 19 | 20 | 22 | 23 | 25 | 24 | mean |
|---|---|---|---|---|---|---|---|---|---|
| Baseline | 10.0 | 9.5 | 10.0 | 10.0 | 10.0 | 10.0 | 10.0 | 10.0 | 9.9 |
| Ex. 3.1 | 8.7 | 9.6 | 9.4 | 7.6 | 9.9 | 8.3 | 7.4 | 9.6 | 8.8 |

TABLE 3.c-continued

Detailed voluntary acceptance test results for the liquid drug-containing formulations according to Ex. 3.1 and 3.2.

| | cats | | | | | | | | |
|---|---|---|---|---|---|---|---|---|---|
| Suspension | 28 | 30 | 29 | 26 | 27 | 31 | 32 | 33 | |
| Baseline | 10.0 | 6.5 | 10.0 | 10.0 | 9.5 | 10.0 | 10.0 | 10.0 | 9.5 |
| Ex. 3.2 | 0 | 0 | 0 | 0 | 0 | 0 | 1 | 0.3 | 0.2 |

Best voluntary acceptance is shown by liquid drug-containing formulations comprising sunflower oil.

The invention claimed is:

1. A method for improving the acceptance or voluntary acceptance of drug intake in an animal comprising administering to the animal a liquid drug-containing formulation comprising:

A) at least one drug, which is a hypoxia-inducible factor prolyl hydroxylase inhibitor, B) at least one natural oil of herbal origin, and C) at least one natural oil of animal origin;

wherein the hypoxia-inducible factor prolyl hydroxylase inhibitor is a compound of formula (I)

(I)

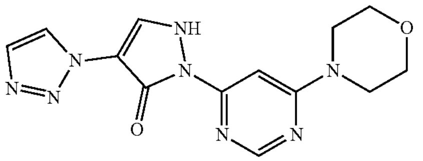

or a salt, stereoisomer, tautomer, or N-oxide thereof;

wherein the liquid drug-containing formulation is administered to a cat;

wherein the liquid drug-containing formulation is administered to a dog; and wherein the acceptance or voluntary acceptance of drug intake is improved over an administration period of at least two weeks.

2. The method of claim 1, wherein the at least one natural oil of herbal origin is almond oil, apricot kernel oil, canola oil, castor oil, coconut oil, cottonseed oil, flaxseed oil, grape oil, hemp oil, maize oil, olive oil, palm oil, peanut oil, sesame seed oil, soya oil, sunflower oil, thistle oil, rapeseed oil, rice bran oil, or wheat germ oil.

3. The method of claim 1, wherein the at least one natural oil of herbal origin is modified almond oil, modified apricot kernel oil, modified canola oil, modified castor oil, modified coconut oil, modified cottonseed oil, modified flaxseed oil, modified grape oil, modified hemp oil, modified maize oil, modified olive oil, modified palm oil, modified peanut oil, modified sesame seed oil, modified soya oil, modified sunflower oil, modified thistle oil, modified rapeseed oil, modified rice bran oil, or modified wheat germ oil, and wherein the modification is alcoholysis.

4. The method of claim 1, wherein the at least one natural oil of animal origin, is fish oil, optionally salmon oil.

5. The method of claim 1, wherein the formulation further comprises a thickener.

6. The method of claim 1, wherein the liquid drug-containing formulation further comprises at least one antioxidant, wherein the antioxidant is ascorbyl palmitate, butylhydroxytoluene, butylhydroxyanisole, citric acid, lecithins, propyl gallate, tocopherol, or a combination thereof; and/or at least one preservative, wherein the preservative is ethanol, propylene glycol, butanol, chlorobutanol, benzoic acid, sorbic acid, para-hydroxybenzoic esters, or a combination thereof; and optionally at least one surfactant.

7. The method of claim 1, wherein the at least one natural oil of herbal origin is soya oil or sunflower oil and wherein at least one natural oil of animal origin is fish oil.

8. The method of claim 1, wherein the at least one natural oil of herbal origin is modified maize oil.

9. The method of claim 5, wherein the thickener is glycerol dibehenate.

10. The method of claim 5, wherein the thickener is glycerol ester.

11. The method of claim 5, wherein the glycerol ester is a glycerol ester with $C_{12}$-$C_{24}$ fatty acids or is a monoester, a diester, a triester, or is a mixture thereof.

12. The method of claim 1, wherein the liquid drug-containing formulation further comprises E) at least one antioxidant selected from the group consisting of ascorbyl palmitate, butylhydroxytoluene, butylhydroxyanisole, citric acid, lecithins, propyl gallate, tocopherol, and combinations of these antioxidants; and/or F) at least one preservative selected from the group consisting of ethanol, propylene glycol, butanol, chlorobutanol, benzoic acid, sorbic acid, para-hydroxybenzoic esters, and combinations thereof; and/or G) optionally at least one surfactant.

13. The method of claim 1, wherein the liquid drug-containing formulation comprises A) the hypoxia-inducible factor prolyl hydroxylase inhibitor in an amount of from 0.1 to 20 wt.-%, optionally from 0.5 to 10 wt.-%, based on the total weight of the liquid drug-containing formulation, B) the at least one natural oil of herbal origin in an amount of from 50 to 99.8 wt.-%, optionally from 70 to 98.97 wt.-%, based on the total weight of the liquid drug-containing formulation, C) optionally the at least one natural oil of animal origin in an amount of from 0.01 to 5 wt.-%, optionally from 0.01 to 1.5 wt.-%, based on the total weight of the liquid drug-containing formulation, D) optionally the at least one thickener in an amount of from 0.1 to 10 wt.-%, optionally from 0.5 to 5 wt.-%, based on the total weight of the liquid drug-containing formulation, E) optionally at least one antioxidant in an amount of from 0.01 to 2 wt.-%, optionally from 0.01 to 1.5 wt.-%, based on the total weight of the liquid drug-containing formulation, and F) optionally at least one preservative in an amount of from 0.01 to 2 wt.-%, optionally from 0.01 to 1.5 wt.-%, based on the total weight of the liquid drug-containing formulation.

* * * * *